(12) United States Patent
Kleven (10) Patent No.: US 6,517,530 B1
(45) Date of Patent: Feb. 11, 2003

(54) PROBE DEVICE

(75) Inventor: Atle Kleven, Trondheim (NO)

(73) Assignee: Leiv Eiriksson Nyfotek AS, Trondheim (NO)

( * ) Notice: Subject to any disclaimer, the term of this patent is extended or adjusted under 35 U.S.C. 154(b) by 0 days.

(21) Appl. No.: 09/297,595

(22) PCT Filed: Oct. 31, 1997

(86) PCT No.: PCT/NO97/00288

§ 371 (c)(1),
(2), (4) Date: Jul. 23, 1999

(87) PCT Pub. No.: WO98/20797

PCT Pub. Date: May 22, 1998

(51) Int. Cl.[7] ............................. A61B 17/00; A61B 8/12
(52) U.S. Cl. ............................. 606/1; 600/439; 600/459
(58) Field of Search ................................. 600/207, 439, 600/459, 462; 606/192, 1

(56) References Cited

U.S. PATENT DOCUMENTS

| | | | |
|---|---|---|---|
| 5,402,772 A | 4/1995 | Moll et al. | 128/20 |
| 5,425,357 A | 6/1995 | Moll et al. | 128/20 |
| 5,431,173 A | 7/1995 | Chin et al. | 606/167 |
| 5,450,843 A | 9/1995 | Moll et al. | 600/20 |
| 5,454,367 A | 10/1995 | Moll et al. | 600/207 |
| 5,465,711 A | 11/1995 | Moll et al. | 600/207 |
| 5,468,248 A | 11/1995 | Chin et al. | 606/192 |
| 5,469,853 A | 11/1995 | Law et al. | 128/662.06 |
| 5,501,653 A | 3/1996 | Chin | 600/204 |
| 5,505,689 A | 4/1996 | Kramer et al. | 600/204 |
| 5,514,075 A | 5/1996 | Moll et al. | 600/202 |
| 5,520,609 A | 5/1996 | Moll et al. | 600/204 |
| 5,522,790 A | 6/1996 | Moll et al. | 600/204 |
| 5,527,264 A | 6/1996 | Moll et al. | 600/204 |
| 5,531,856 A | 7/1996 | Moll et al. | 156/290 |
| 5,562,603 A | 10/1996 | Moll et al. | 600/204 |
| 5,569,165 A | 10/1996 | Chin et al. | 600/204 |
| 5,575,759 A | 11/1996 | Moll et al. | 600/207 |
| 5,632,761 A | 5/1997 | Smith et al. | 606/192 |
| 5,634,883 A | 6/1997 | Chin et al. | 600/204 |
| 5,643,178 A | 7/1997 | Moll et al. | 600/204 |
| 5,690,607 A | 11/1997 | Chin et al. | 600/228 |
| 5,704,372 A | 1/1998 | Moll et al. | 128/898 |
| 6,086,528 A | * 7/2000 | Adair | 600/104 |
| 6,099,464 A | * 8/2000 | Shimizu et al. | 600/104 |

FOREIGN PATENT DOCUMENTS

WO   WO 92/21298   12/1998   ........... A61B/17/32

* cited by examiner

Primary Examiner—Francis J. Jaworski
(74) Attorney, Agent, or Firm—Duane Morris LLP (57) ABSTRACT

Probe device having an auxiliary element for use during surgery where there is employed a surgical instrument (40) of the type comprising a relatively elongate, rod-shaped member being provided with a work element (41) at its outer, free end. A sleeve-shaped main part (1) is adapted to be mounted around the rod-shaped member of the instrument and is provided with the auxiliary element (5) at its one end, corresponding to the outer, free end of the rod-shaped member. The main part (1) is slideable in its longitudinal direction between two extreme positions, namely a retracted and a forward position, with a resulting altered position of the auxiliary element (5) in relation to the work element (41).

11 Claims, 8 Drawing Sheets

PROBE DEVICE

This invention relates to a probe-device having an auxiliary element for use during surgery, where there is employed a surgical instrument of the type comprising a relatively elongate, rod-shaped member being provided with a work element at its outer, free end. An auxiliary in this connection can be a sensor element for the detection of physiological parameters, or as an alternative the auxiliary can be an instrument or tool element intended for active use by the surgeon during the operation. Thus in principle this latter form of auxiliary can be of a similar type as the work element referred to at the surgical instrument with which the probe device is adapted to cooperate.

In the following description a starting point has mainly been taken in a device having an auxiliary element of the first mentioned type, namely a sensor element e.g. in the form of an ultrasonic transducer. In general there can here be the question of sensors for detection of various physiological parameters (such as pulse, blood pressure, oxygen saturation and so forth) and physiological structures (blood vessels) during an operation carried out with endoscopic or other tecniques.

It is considered in this connection that the surgical instrument with which the probe device can be associated or cooperate, can be a surgical instrument of a standard type, which inherently is designed to be used by the surgeon during operations without being assisted by the specific probe device according to the invention.

This probe device can be employed in most situations where a surgical instrument, being either rigid or flexible, is already employed during an endoscopic operation. Endoscopic and laparoscopic surgical methods have been much developed during recent years. More and more operations are carried out with endoscopic techniques, which today are based on rigid or flexible instruments controlled by the operator by means of light optics in the endoscopes. In laparoscopic operations it is necessary to introduce several instruments simultaneously through several small openings (ports) in the abdominal wall. Light and optics then have a dedicated port and the surgical instruments are used in from one to four extra ports.

The situation today is such that usually there are not employed probes or instruments for detecting physiological parameters during endoscopic operations. The reason is that the surgeon is reluctant to introduce still another surgical tool into the work field. If this tool is to be available at any time it must be introduced through a separate port. It is desired to keep the number of ports at a minimum, so as to ease the patient's trauma and increase the safety of the operation. To dedicate a separate port for an instrument for physiological parameter determination, is not considered to be expedient during standard procedures where the duration of the operation has great importance. If such an instrument shall be used during an operation where there is not allocated any dedicated port, it will be necessary to perform a change from surgical instrument to detection instrument in one of the ports. This is a time-consuming process. It is desirable to have as few instrument changes as possible in order to keep the operation time short. Endoscopic techniques involve the possibility of the surgeon to have palpating contact with physiological structures. In order to maintain safety margins the surgeon will proceed very carefully and let further work be based on visual verification of the physiology through the light and video channels of the endoscopes. It is a cumbersome work and a time-consuming process to expose all structures for verification before the surgical procedure can proceed. This is a time-consuming process. When using an instrument for detecting physiological parameters, such as blood vessel detection, the verification of structures lying underneath, can be made before visual verification is possible. The endoscopic procedures can be performed more quickly and safely, which saves the patient for great strain in connection with long operations and a long convalescense time. This leads to cost effective savings.

Thus it is a general object of the invention to provide a probe device which together with a surgical standard instrument constitutes a simple and very useful tool unit at the disposal of the surgeon, so that the surgeon in situations as discussed above, in a more simple manner and more easily can carry out difficult steps during an operation. In this connection it is also very important that the probe device makes possible very inexpensive solutions, taking into account among other things that common surgical standard instruments are taken as a basis.

Previously known methods and techniques of interest in this context, can be considered to be represented by the following patent specifications:

[1] U.S. Pat. No. 5,325,860
[2] U.S. Pat. No. 5,353,783
[3] U.S. Pat. No. 5,275,166
[4] U.S. Pat. No. 5,413,107

Aspects of technological methods for detecting blood vessels are known from other clinical connections and purposes. Ultrasound doppler and ultrasound imaging are described for the purpose of detecting blood vessels in time and to be able to clamp these during laparoscopic operations [3]. An ultrasound system is located on an endoscopic instrument dedicated for blood vessel detection or in combination with a clamping tool or the like. There is described a catheter whereby ultrasound imaging monitors a surgical instrument introduced through the lumen of the catheter [1]. A laparoscopic ultrasound imaging instrument having a flexible tip is described for dedicated ultrasound imaging of a surgical region [4]. A surrounding hose is described for use outside an existing endoscope [2]. The hose serves as a sterile protection for the endoscope and in addition contains several external foldable work channels for introducing endoscopic tools.

On the above background the novel and specific features of the probe device according to the invention in the first place consists in a sleeve-shaped main part adapted to be mounted externally of the rod-shaped member of the instrument, being either rigid or flexible, and provided with the auxiliary element at one end, corresponding to the outer free end of the rod-shaped member, said main part being slideable in its longitudinal direction between two extreme positions, namely a retracted and an extended or forward position, with a resulting altered position of the auxiliary element in relation to the work element.

In a typical practical embodiment based on the invention, this novel probe device thus comprises a main part or supporting part in the form of a sleeve at the end of which there is mounted one or more sensors for detection. This sleeve can be threaded onto a standard endoscopic surgical instrument, as a supplement to the function thereof. The sleeve can be threaded so far onto the surgical instrument that during normal work conditions it is outside the field of work of the surgical instrument. When situations occur, where it is important to investigate the surgical region concerned, with respect to measurable physiological parameters given by the sleeve sensor or sensors, the sleeve can be moved forwardly along the surgical instrument by means of a release mechanism, so that the sensor or sensors enter into the field of work. When parameter determination has been finished the sleeve is retracted along the instrument and out of its field of work.

The present invention makes its possible to combine any endoscopic instrument with a probe for detecting physiological parameters or detectable physiological structures. The surgeon selects which of the endoscopic instruments it is suitable to provide with this auxiliary function. The surgeon will have the opportunity to increase safety during the operation, by being at an early stage able to verify hidden physiological structures, and to shorten the intervention time without introducing a dedicated port and without exchanging the instruments in the ports more frequently. In this context emphasis is put on the significance and the advantage of having a trigger function as will be described with reference to the drawings. Thus the surgeon does not have to give away possible other instruments from the other hand in order to change the sleeve position on the endoscopic instrument. This is particularly important when the surgeon holds the video-light endoscope in one hand and manipulates a surgical endoscopic instrument with the other hand. There is no room for laying away any of the instruments in order to activate the auxiliary function.

The method is of interest in most surgical branches where there are employed endoscopic or endoscope-like techniques such as laparoscopic surgery, gastroscopic surgery, bronchoscopy, urology etc. All methods based on rigid or flexible endoscopic instruments can, by means of the probe device according to the invention, suitably be supplied with a detection function, such as e.g. blood vessel detection, with a threadable probe device having one or more sensor elements.

As a summary of the above, introductory description, the probe device according to the invention can in many practical and favourable embodiments, comprise the following important features:

A thin flexible sleeve of a suitable bio-compatible material, acting as a supporting member for a sensor element, having an inner diameter adjusted so that the sleeve can be mounted onto existing flexible or rigid endoscopic instruments.

A flexible tip at the end of the supporting member, being angularly set at 90° from the longitudinal direction of the supporting member when this has not been pulled over an endoscopic instrument. When an endoscopic surgical instrument is introduced into the supporting member and is extended through it, the flexible tip will be straightened out and will be lying flush with the surface of the supporting member.

At least one sensor element located on the flexible tip at the end portion of the supporting member. The sensor element is adapted to detect physiological parameters or physiological structures in and adjacent to the work region of the endoscopic instrument, when the flexible tip has been extended in relation to the endoscopic instrument introduced therein.

An associated channel in the supporting member and the flexible tip for extending an electrical-optical connection to the sensor element.

A lock and trigger mechanism attached to the other end of the supporting member, for manipulation thereof and thereby the position of the sensor element on the endoscopic instrument. The lock and trigger mechanism can be mounted permanently to the supporting member or can consist of a unit for use with several disposable sleeves.

An electronics unit can be connected to the sensor element for delivering an operator signal upon detection of physiological parameters or physiological structures.

The invention as well as additional particular features and advantages thereof, will be explained more closely in the following description with reference to the drawings, wherein:

FIG. 1 schematically shows an example of a probe device according to the invention, FIG. 2 in perspective view and much enlarged shows details of a flexible bending portion at the outer free end of the device (at the right-hand side) of FIG. 1, FIG. 3 somewhat more detailed than FIG. 1 shows a lock and trigger mechanism at the inner end of the device, i.e. the opposite end of what is illustrated in FIG. 2, FIGS. 4a and 4b show the probe device in FIG. 1 as mounted on an endoscopic surgical instrument of a common standard type, (FIG. 4a) with the probe device retracted and (FIG. 4b) with the probe device in a forward position, respectively, FIGS. 5a and 5b in schematical vertical section and horisontal section respecively, show an alternative embodiment of the trigger mechanism.

Figure 1:
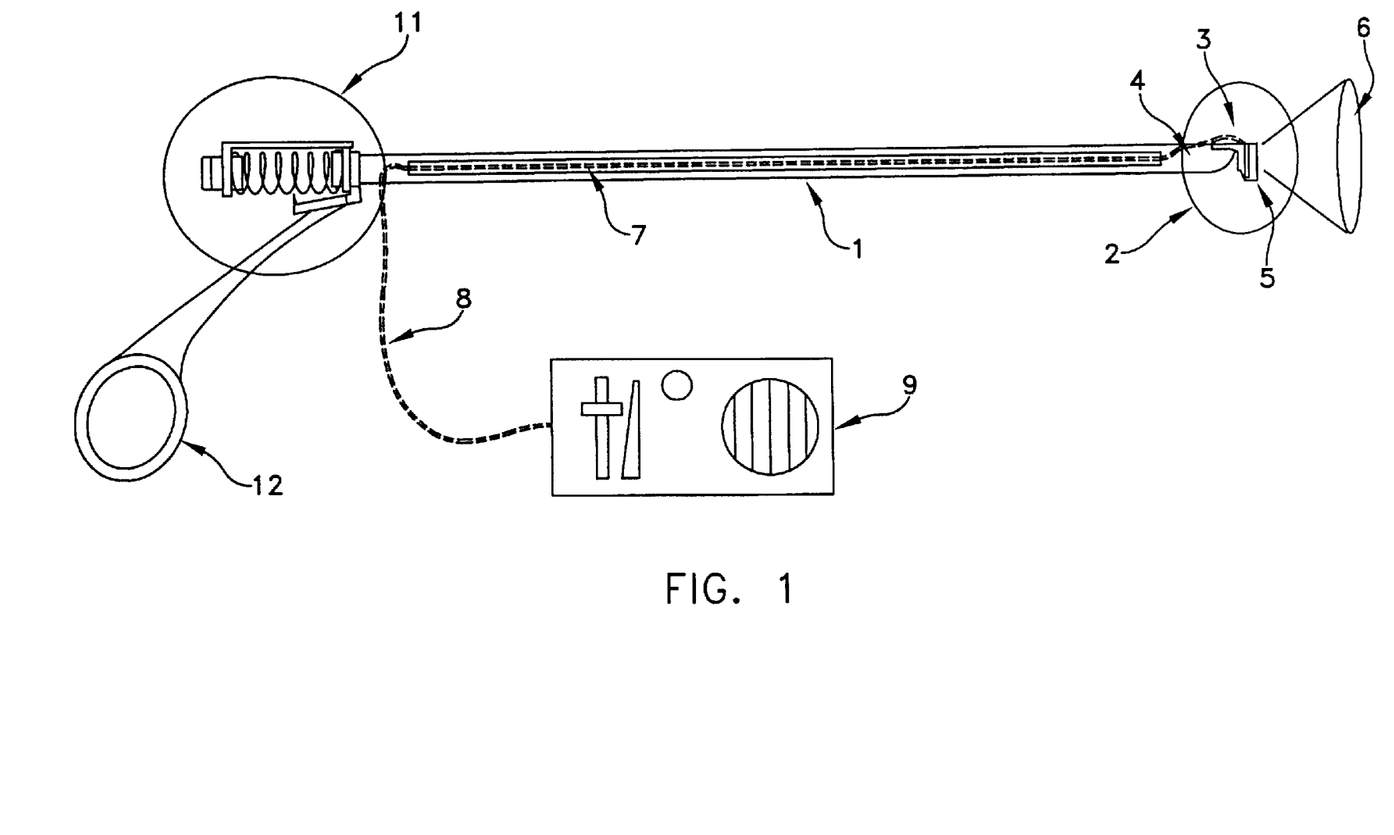

FIG. 1 shows a probe device with a supporting main part in the form of a sleeve-like, bio-compatible tube 1 with thin walls. The stiffness of the tube is so adjusted that it can be pushed on an endoscopic surgical instrument without being deformed. At the outermost part of the tube cross-section 1 a portion of the tube has been removed so that the tip 2 will be particularly flexible. The resulting junction part 3 between tube 1 and tip 2 is formed with a spring function (e.g. with a leaf spring 4 incorporated therein). This spring is bent 90° in a rest position and is so mounted that tip 2 normally is bent 90° radially inwards in relation to the longitudinal direction of tube 1. At tip 2 there is mounted at least one sensor 5 at the surface of tube 1. The detection field 6 of sensor 5 is normally directed forwards in the longitudinal direction of tube 1. In tube 1 there is shown a channel 7 with space for electrical connection 8 of sensor element 5 to an electronics unit 9, for delivering an operator signal during detection and localisation of physiological parameters and structures. At the inner end of tube 1 there is mounted a trigger 12 and a release mechanism 11 having for its function to control the position of tube 1 and thereby sensor element 5 on the surgical instrument.

The electronics unit 9 as shown in FIG. 1, constitutes per se no part of the actual probe device, and can contain conventional circuits for desired functions in connection with the operator signal mentioned.

Figure 2:
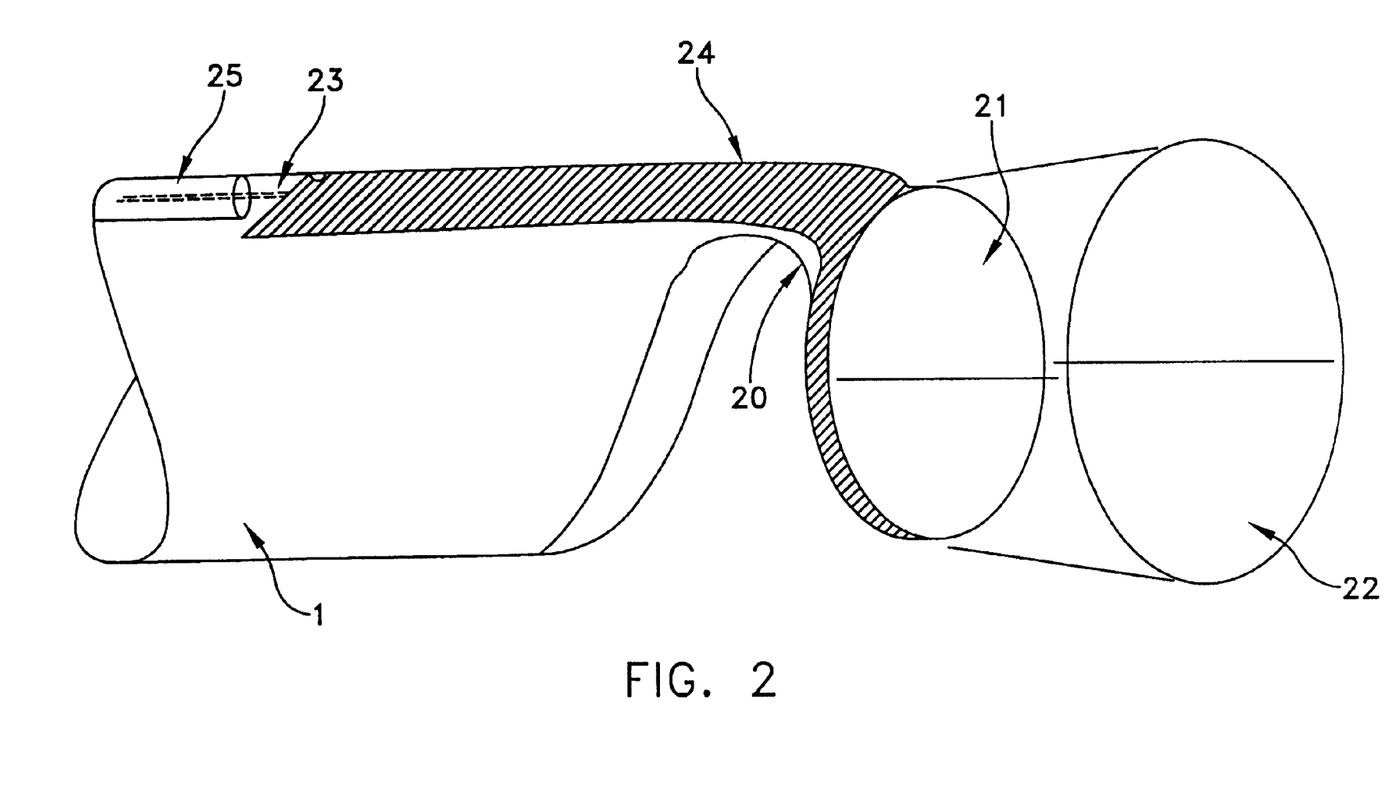

FIG. 2 shows more in detail the flexible tip 2 in FIG. 1. The bio-compatible, flexible and thin-walled tube 1 is so shaped that the tip forms a particularly bendable part 20. This junction part 20 corresponds to the bendable part 3

(FIG. 1) of tube 1. At the upper side of tube 1 there is provided a spring 24 (leaf spring, spiral spring, recilient plastic material, memory metal, memory plastic). This spring 24 in "rest position" is shaped as an L. Spring function 24 bends the flexible part 20 by 90° inwards towards the center of tube 1, so that the normal on the surface of the bendable part 20 points in the longitudinal direction of tube 1. At the surface of the bendable part 20 there is mounted at least one sensor 21. The detection field 22 of sensor 21 is oriented in the longitudinal direction of tube 1. Sensor element 21 is electrically or optically connected to the sensor electronics 9 (FIG. 1) through a conductor 23. The conductor is extended through a channel 25 in tube 1.

Figure 3:
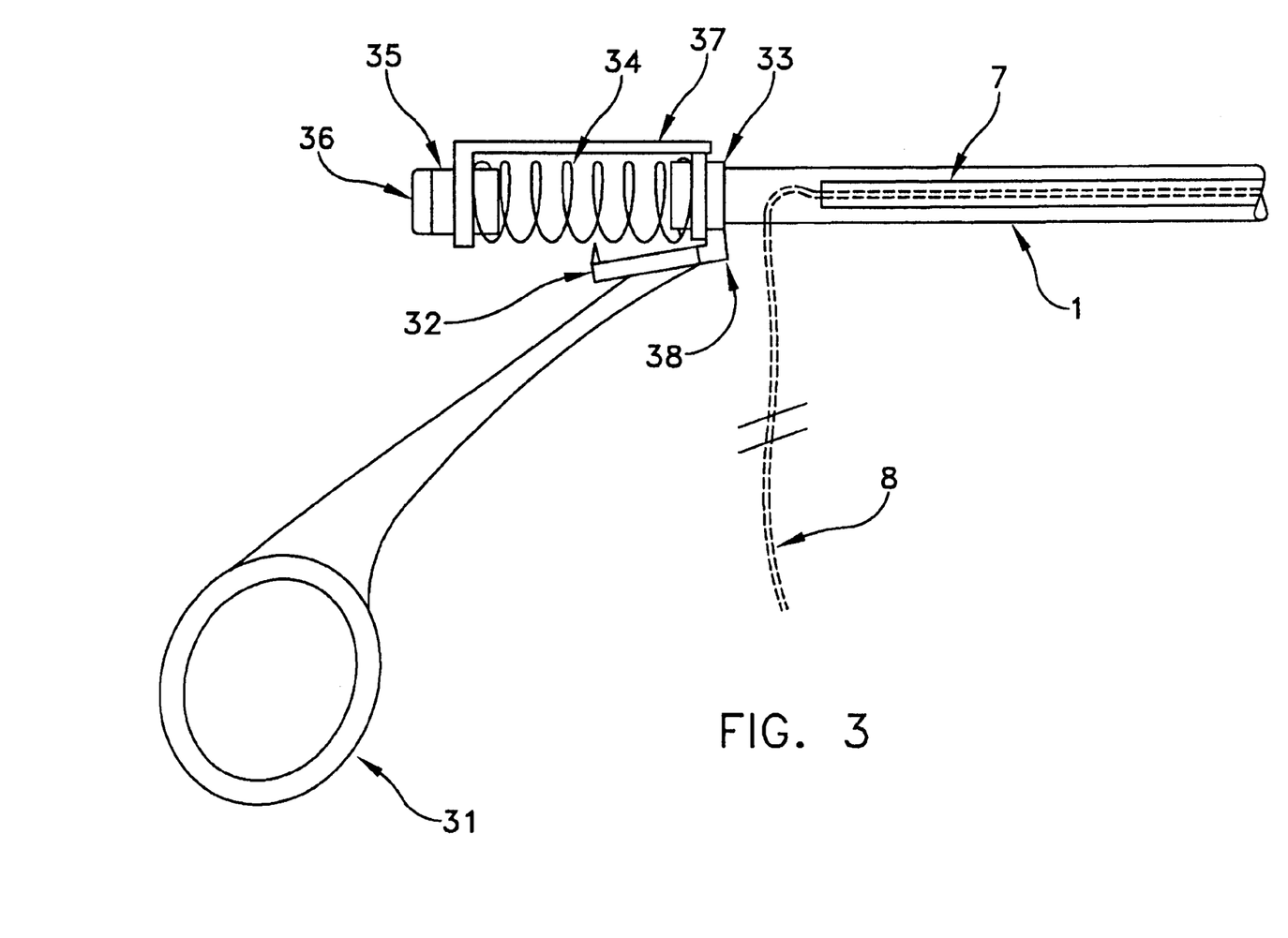

FIG. 3 shows a detail of a fundamental method of controlling the movements of tube 1 on the endoscopic surgical tool. At the inner end of the bio-compatible, flexible and thin-walled tube 1 there is attached a mechanism 11,12 (FIG. 1) for controlling the movement of the supporting member on the surgical tool. A trigger 31 with a hook 32 is attached to the tube 1 with a flexible, resilient coupling 38. Directly to the end of tube 1 there is attached a span piece 33 with a through hole of the same diameter as the cavity in tube 1. On the span piece there is mounted a spring 34. At the other end of spring 34 there is located a span piece 35 with a through hole having a diameter corresponding to the cavity in tube 1. At the end of or inside span piece 35 there is mounted a friction lock 36 (O-ring or similar) of an inner diameter being a little smaller than the cavity of tube 1. Friction lock 36 will lock trigger mechanism 11,12 (FIG. 1) to the surgical instrument. On span piece 35 there is mounted an expansion stop 37 with a hook preventing spring 34 from expanding more than a predetermined length. This length corresponds to the distance that the sensor element must be moved in order to be free from the endoscopic surgical instrument.

Figure 4A:
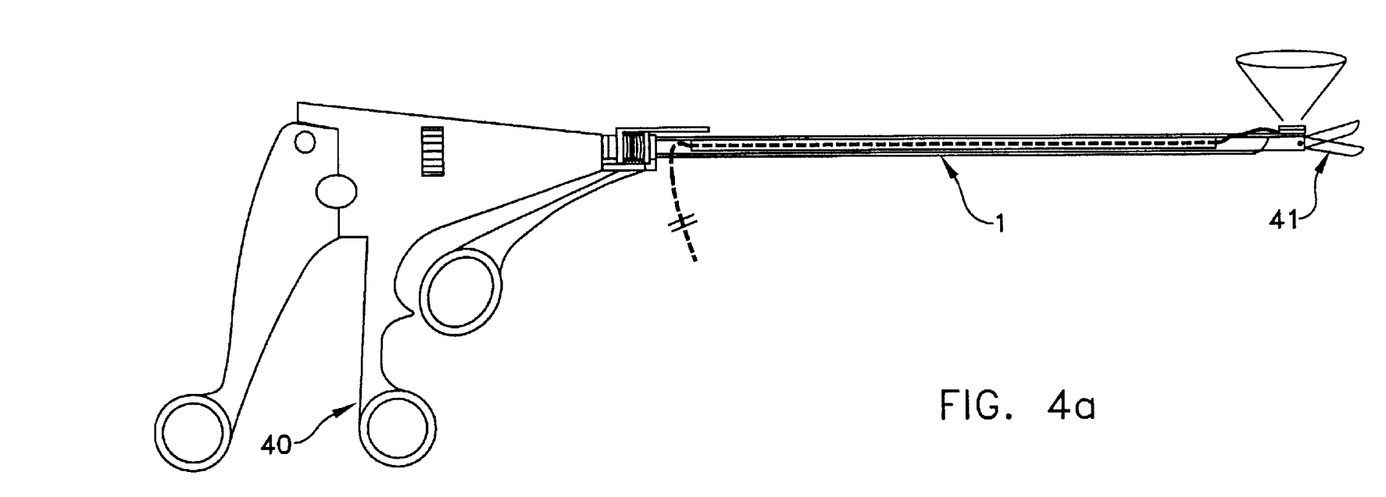
Figure 4B:
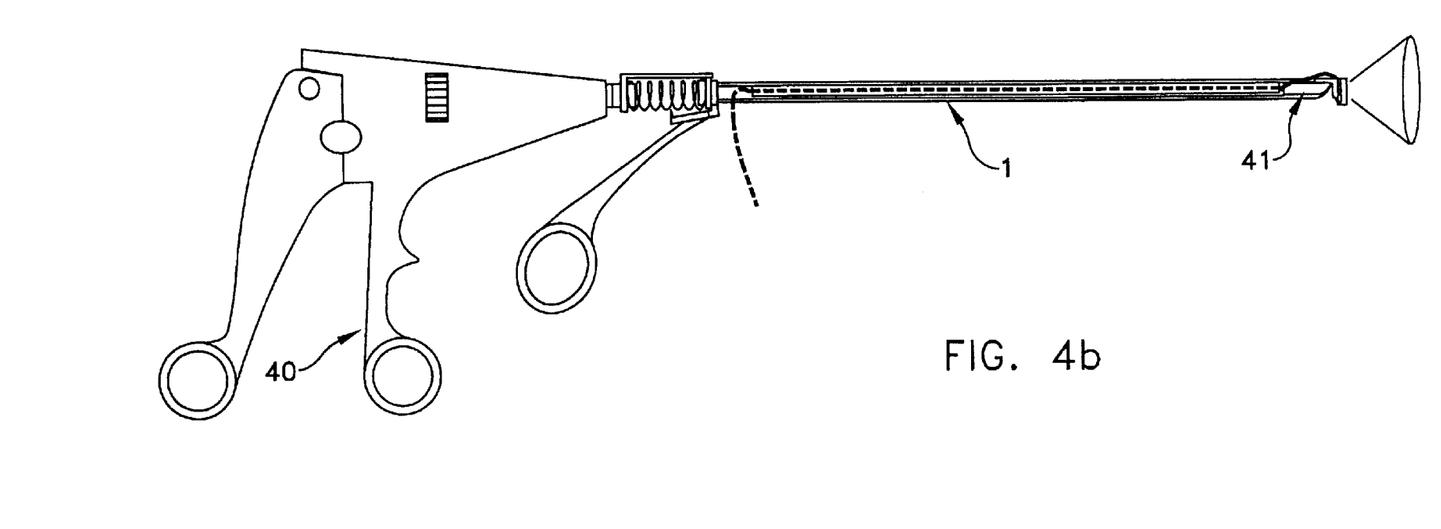

FIGS. 4a and 4b show a probe according to the invention mounted on a standard endoscopic surgical instrument 40. The rod-shaped member of the surgical instrument 40 is inserted through friction lock 36 (FIG. 3), span piece 35, spring 34, span piece 33 and tube 1. FIG. 4a shows the sleeve- or tube-shaped main part 1 in a retracted position. When spring 34 (FIG. 3) is compressed and locked in this position by means of hook 34 against span piece 36, the length of tube 1 is so adjusted that the surgical instrument extends completely through tube 1 and the work tool 41 of the instrument is free at the end of tube 1. In this situation the surgical instrument 40, which fills the cavity of tube 1, will press the bendable part 20 (FIG. 2) outwards and spring 24 will be straightened out. Then the surface of sensor element 21 will be parallel to the longitudinal axis of tube 1 and the field of the sensor element will be directed noramlly to the longitudinal axis of tube 1. The tool on the surgical instrument 40 is now free and available for use. In FIG. 4b the trigger 31 (FIG. 3) has been pushed down so that hook 32 is released from span piece 35. Spring 34 expands and pushes span piece 33, trigger 31 with hook 32 and tube 1 outwards along the longitudinal direction of the surgical instrument 40. When spring 34 expands, the tip 2 of tube 1 (FIG. 1) will pass by the tool end 41 of the surgical instrument. The bendable part 20 (FIG. 2) will become free and spring 24 will bend the bendable part 20 down to the initial position at 90° to the longitudinal direction of tube 1. The normal to the surface of sensor element 21 (FIG. 2) is now parallel to the longitudinal direction of tube 1 and the field of sensor element 21 is directed in the same direction. In this position sensor element 21 (FIG. 2) is ready for its function and detection of physiological parameters or physiological structures can suitably be performed. When detection has been finished, trigger 31 (FIG. 3) is pulled back so that the tool element of the surgical instrument again will become free of the cavity of tube 1. Sensor element 21 (FIG. 2) can also be active in this situation (FIG. 4a) so as to be able to detect structures lying normal to the longitudinal direction of the surgical tool 40.

Above there has mainly been the question of two positions of the sensor element 21, made possible by the bending part referred to, but it will be realized that the tip of the sleeve- or tube-shaped main part 1 of the probe, can also be set in one or more intermediate positions depending on the functions desired. Here there may be the question both of a number of fixed positions, indicated e.g. by snap effect, or a completely stepless or continuous adjustment over the whole angular range made possible by the bending part. The device will be most reliable in the majority of cases, when the tip is adapted to assume two well defined extreme positions at the choice of the surgeon.

Figure 5A:
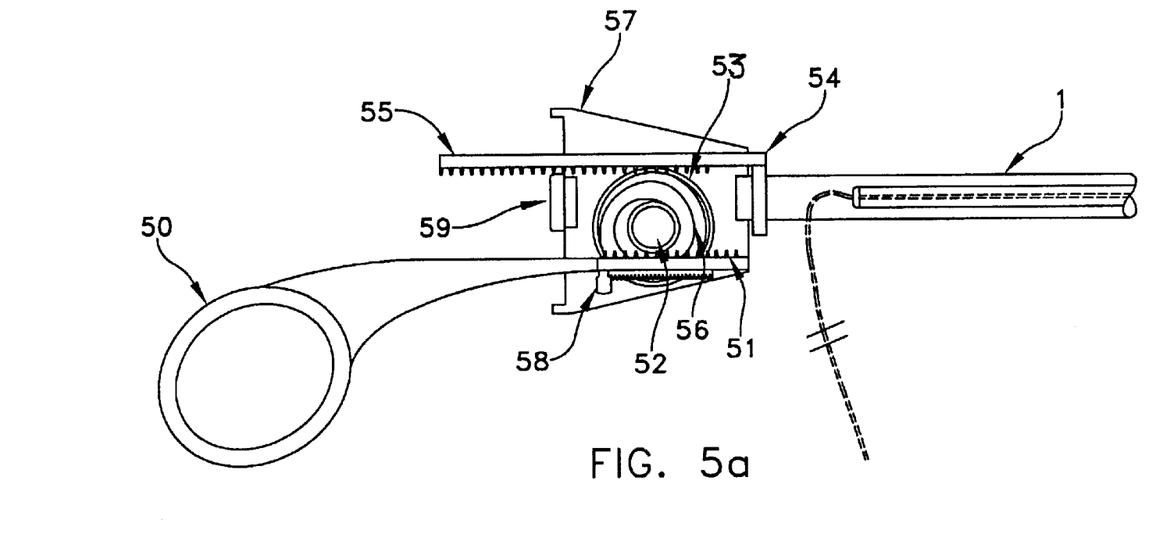
Figure 5B:
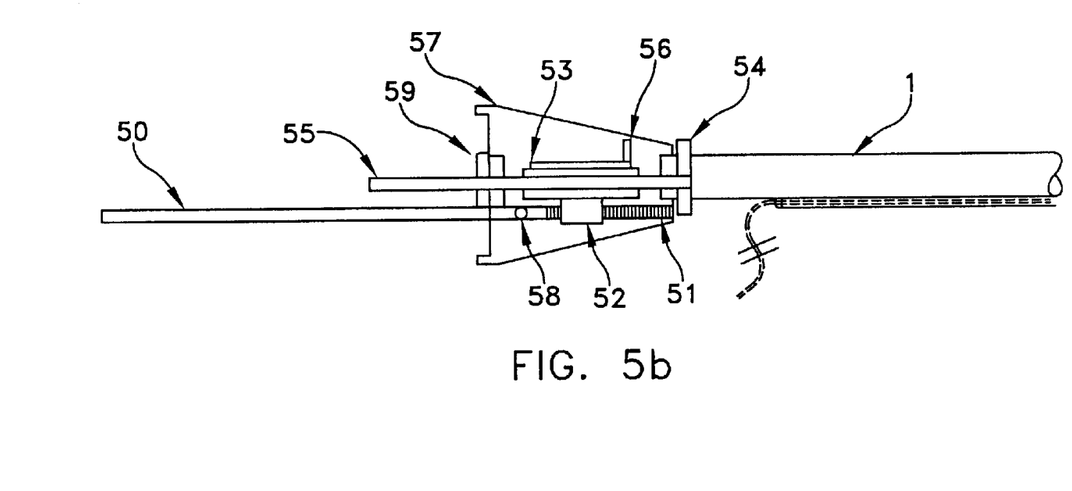

FIGS. 5a and 5b show a trigger and locking mechanism having av ratio of transmission between the movement of the trigger 50 and the movement of tube 1 outwards on the surgical instrument (not shown). On trigger 50 there is mounted a toothed rack 51 being in engagement with a small gear 52. Gear 52 is axially coupled to a larger gear 53. At tube 1 there is attached an end piece 54 with a toothed rack 55. Rack 55 engages the large gear 53. FIG. 5a shows sleeve 1 in a retracted position (see FIG. 4a). If trigger 50 is pulled in the opposite direction of the tip 2 of tube 1 (FIG. 1), rack 51 will transmit force to gear 52 that will rotate together with gear 53. Rack 55 is thereby moved in the opposite direction of rack 51 and pushes sleeve 1 out on the surgical instrument so that sensor element 21 (FIG. 2) will arrive at a forward, active position (FIG. 4b). Because of the ratio of transmission between the small gear 51 and the large gear 53, a relatively small movement of trigger 50 will be sufficient for moving sleeve 1 from the retracted position (FIG. 4a) to the projected position (FIG. 4b). A spring 56 is attached to the axle between gear 51 and gear 53. Spring 56 is anchored in trigger housing 57. When the trigger 50 is spanned and gears 51, 53 are rotated, spring 56 will be tightened. In order that the covering sleeve 1 shall come into the retracted position, trigger 50 is released and spring 56 will be slackened so that sleeve 1 is pulled back over the surgical instrument. There is mounted an adjustable locking mechanism 58 on the trigger so that sleeve 1 can be locked in a more or less projected position (FIG. 4b), possibly in a stepless manner. At the rear end of trigger housing 57 there is a hole for introducing the surgical instrument. In the hole there is inserted a friction lock 59 being so adjusted that the locking and trigger mechanism is sufficiently well attached to the surgical instrument when this is introduced into sleeve 1.

Figure 6:
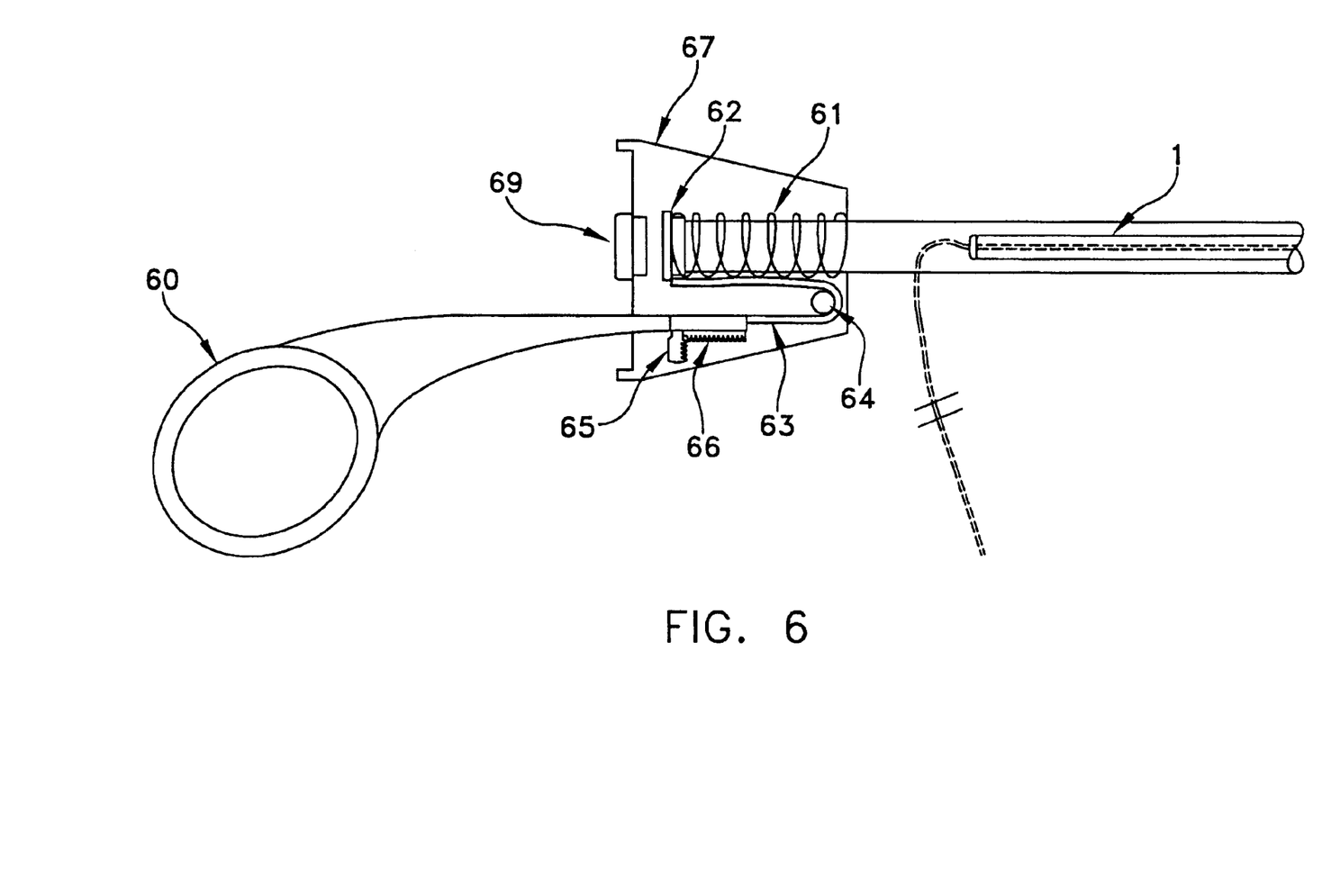
FIG. 6 shows a further alternative embodiment of the trigger mechanism, being somewhat simplified in relation to the preceding embodiments.

FIG. 6 shows a simpler version of the locking and trigger mechanism compared to the one in FIG. 5. At the inner end of sleeve 1 there is mounted a spring 61 being in engagement against trigger housing 67 and a span piece 62 being fixably mounted to the end of sleeve 1. Sleeve 1 is not permanently mounted in trigger housing 67. To span piece 62 there is attached a wire (or similar) being passed via a pully to trigger 60. If the trigger 60 is pulled in a direction away from the active tip of the instrument, the wire will transfer the force to sleeve 1, which is pushed outwards on the surgical instrument (not shown). Spring 61 is spanned. On trigger 60 there is mounted an adjustable locking mechanism 65, 66 so that trigger 60 can be locked in a preferably stepless manner in extreme positions and thereby also lock tip 2 of the sleeve (FIG. 1) and sensor element 5 (FIG. 1) in a forward position. In the rear end of trigger housing 67 there is a hole for introducing the surgical instrument (not shown). In the hole there is inserted a friction lock 69 being so adjusted that the lock and trigger mechanism is sufficiently well attached to the surgical instrument when this has been introduced into sleeve 1.

Figure 7:
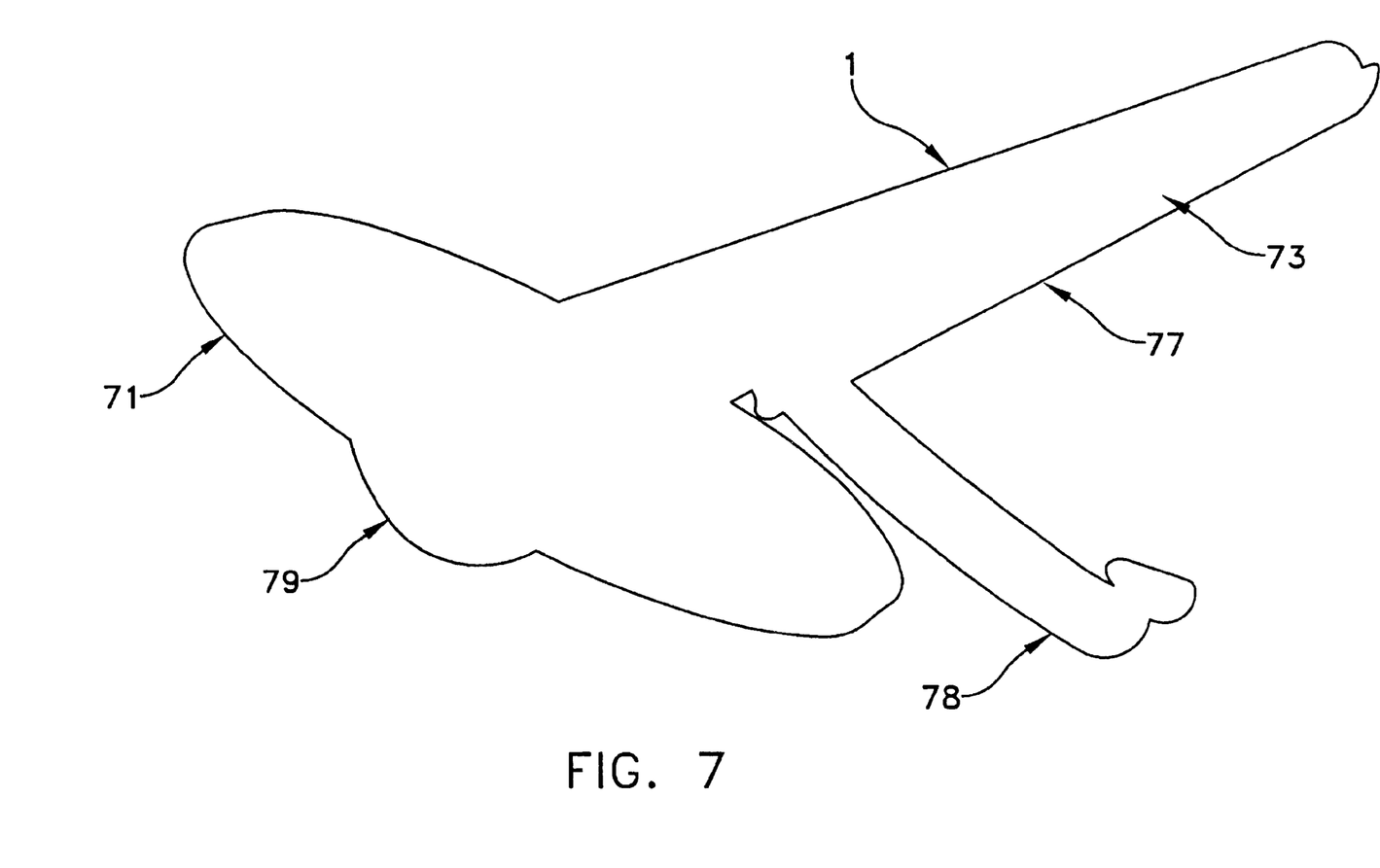
FIG. 7 shows an additional, simplified design for purely manual and direct displacement of the probe device on a surgical standard instrument (not shown), FIG. 8a in a similar way and enlarged as in FIG. 2, shows an embodiment of the probe wherein at the tip there is provided an active auxiliary element in the form of bipolar diathermy electrodes, and FIG. 8b also shows a type of active auxiliary element based on e.g. laser radiation, and without the flexibility being characteristic to embodiments in the above figures of drawings.

FIG. 7 shows the sleeve device 1 with a grip 71 and lock ring 79, channel 77 for electrical or optical connection of one or more sensor elements and the connecting wire 78 between sensor element and electronics for the operator signal. Grip 71 makes it possible to push the sleeve device 1 purely manually in the longitudinal direction of an endoscopic surgical instrument. Friction lock 79 is made of a soft material and has an inner diameter adjusted so that it is a little smaller than the diameter of the surgical instrument being introduced into sleeve 1.

FIG. 7 also shows how the length of sleeve 1 can be adjusted in relation to the length of the surgical instrument. Sleeve 1 is detachable from grip 71 and lock ring 79 by means of a type of quick coupling between tube 1 and grip 71. Supply channel 77 has a longitudinal perforated tear edge 73. For making the length of sleeve 1 shorter, connection wire 78 is torn loose from the supply channel 77 until the length desired of sleeve 1, has been reached. Then it is cut just above the place where connection wire 78 comes out of supply channel 77. Then sleeve 1 is mounted with the quick coupling to grip 71 and the probe is ready for use after this adjustment of the sleeve length according to the rod member of the surgical instrument concerned.

Figure 8A:
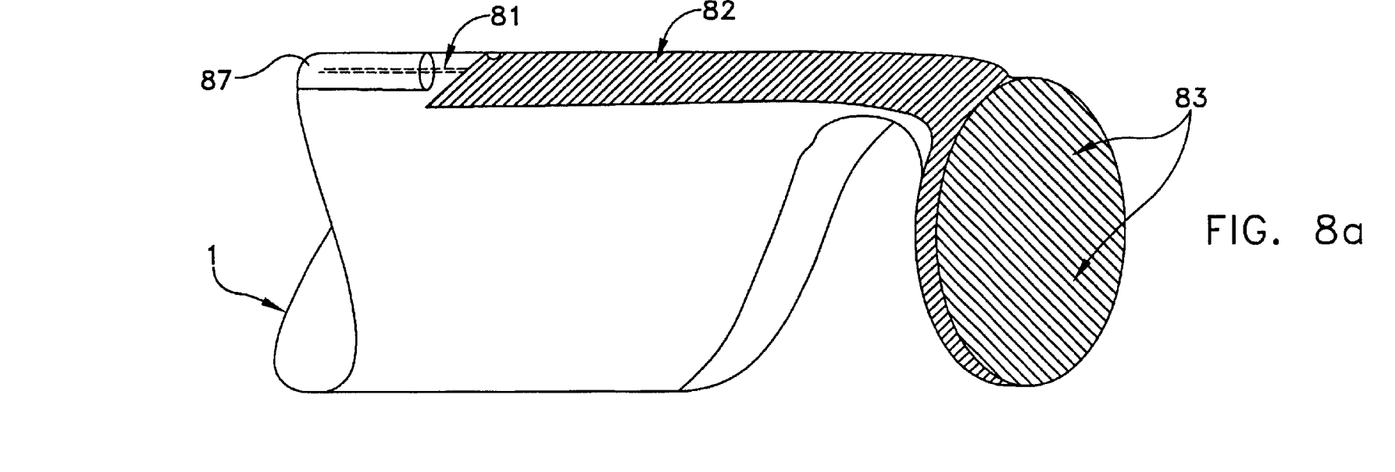
Figure 8B:
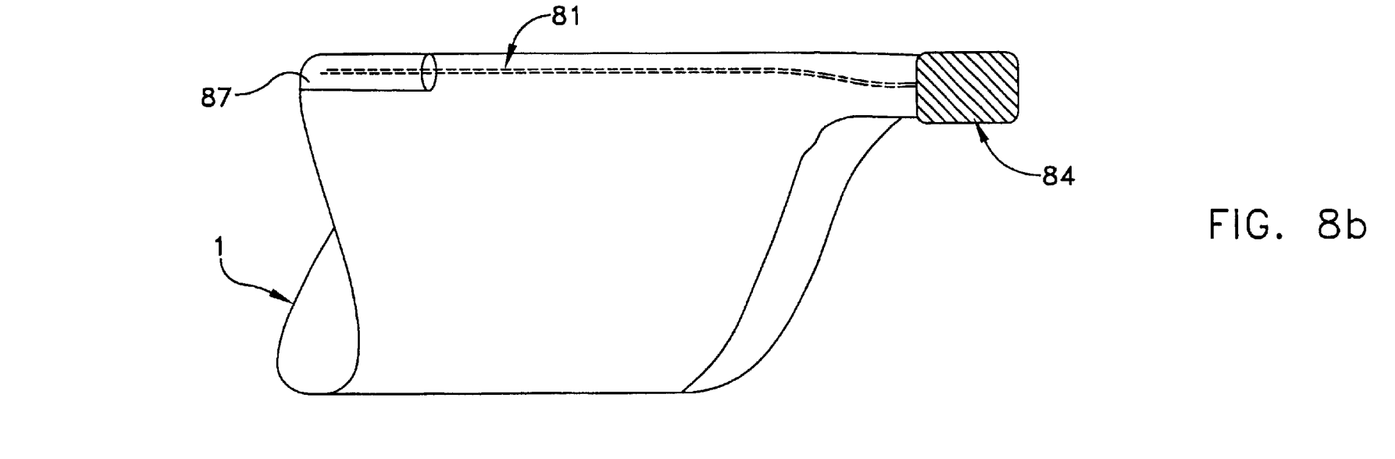

FIGS. 8a and 8b show possibilities of providing the sleeve device 1 with various types of active auxiliary elements. In FIG. 8a sensor element 21 (FIG. 2) has been replaced by bipolar diathermy electrodes 83. Electrical connection takes place by means of wires 81 being extended up to the electrodes through supply channel 87. As in FIG. 2 there is here shown an inserted spring element 82 for a corresponding bending effect as discussed above.

Diathermy is much used during endoscopic techniques for coagulating small blood vessels. Not all standard endoscopic surgical instruments have built-in diathermy electrodes. A universal add-on possibility with diathermy for any endoscopic instrument gives the surgeon much flexibility in the choice of instruments. Besides the number of ports to the surgical region can be limited.

FIG. 8b shows another type of auxiliary element mounted on sleeve 1. Spring element 24 has been omitted and an actuator 84 is mounted on a rigid prolongation 85 of sleeve 1. This actuator 84 can be a laser lens for cutting or removing tissue or coagulation of blood and veins. Laser light is conducted by the optical supply conductor 81 through supply channel 87. Other types of active actuators that may be contemplated for mounting as in FIG. 8b, are tool or work elements for monopolar diathermy, ultrasound cutting (knife) and RF-ablation (antennaes).

From the above description with reference to the drawings it appears that the fundamental solution according to the invention, with a separate and replaceable probe device for selectable mounting on various types of surgical standard instruments, can be designed in many practical variants, from the more simple embodiments as e.g. illlustrated in FIGS. 7 and 8b, to embodiments having more automatically operating lock and release mechanism as well as bending properties, as e.g. illustrated in FIGS. 2–5. A combined tool unit consisting of a surgical standard instrument to which is mounted a probe according to the invention, can also be employed without an endoscope having an associated work channel, whereby according to the circumstances the combination tool can be introduced by the surgeon directly in the operation opening or cavity. As regards the actual mounting of the probe device on the surgical instrument concerned, this can also take place in that the elongate, rod-shaped member of the instrument is separable from the actual instrument handle, so that the rod member can be inserted into the sleeve-shaped main part of the probe through a mouth or opening presented by the cavity thereof at the outer free end referred to above. The main part is adapted to be exchangeable in relation to one or more surgical standard instruments and preferably is intended for use only once.

What is claimed is:

1. A probe device having an auxiliary element for use during surgical operations where there is employed a surgical instrument of the type comprising a relatively elongate, rod-shaped member provided with a work element at an outer, free end thereof, further comprising a sleeve-shaped main part adapted to be threaded onto the rod-shaped member of the instrument and provided with said auxiliary element at said outer, free end of said rod-shaped member, said main part being slideable in the longitudinal direction between two extreme positions, namely a retracted position and a forward position, so as to alter the position of said auxiliary element in relation to said work element wherein the main part is provided with a spring-actuated release mechanism with a finger grip as a trigger or operating means.

2. Device according to claim 1 wherein said auxiliary element is a sensor element being carried by a flexible bending part at one end of the main part, so that the sensor element is acted upon by the rod-shaped member and/or the work element in the retracted position, to assume a first angular and inactive position and in a forward position another angular and active position in front of the work element.

3. Device according to claim 2 wherein the bending part comprises a spring element adapted to press the sensor element to said other angular position.

4. Device according to claim 2 wherein the sensor element in the active angular position is adapted to at least one of sense or cover a region being generally axially forwardly in the longitudinal direction of the main part.

5. Device according to claim 2 wherein the sensor element is an ultrasonic transducer adapted for blood vessel detection.

6. Device according to claim 2 wherein the sensor element is heat sensitive.

7. Device according to claim 1 wherein the main part is directly manually slideable by means of a finger grip portion formed on the main part at a distance from said one end.

8. Device according to claim 1 wherein the trigger mechanism for a detachable coupling for anchoring of the main part and an axial through passage with friction lock effect, for cooperation with said rod-shaped member of the surgical instrument.

9. Device according to claim 1 wherein the main part is adapted in a stepless manner to assume intermediate positions between the two extreme positions.

10. A probe device having an auxiliary element for use during surgical operations where there is employed a surgical instrument of the type comprising a relatively elongate, rod-shaped member provided with a work element at an outer, free end thereof, further comprising a sleeve-shaped main part adapted to be threaded onto the rod-shaped member of the instrument and provided with said auxiliary element at said outer, free end of said rod-shaped member, said main part being slideable in the longitudinal direction between two extreme positions, namely a retracted position and a forward position, so as to alter the position of said auxiliary element in relation to said work element wherein the main part has a length and a tearable electrical wire such that along a length portion opposite to said one end, said tearable electrical wire can be cut off for adjustment to the rod-shaped member of the surgical instrument.

11. Device according to claim 10 wherein the main part is adapted in a stepless manner to assume intermediate positions between the two extreme positions.

* * * * *